United States Patent [19]

Schneider

[11] Patent Number: 5,578,023
[45] Date of Patent: Nov. 26, 1996

[54] FLUSH-INTERVAL INDICATOR FOR SOLUBLE POUCHES

[75] Inventor: Barry L. Schneider, McHenry, Ill.

[73] Assignee: Hollister Incorporated, Libertyville, Ill.

[21] Appl. No.: 372,043

[22] Filed: Jan. 12, 1995

Related U.S. Application Data

[62] Division of Ser. No. 184,220, Jan. 18, 1994, Pat. No. 5,403,299.

[51] Int. Cl.$^6$ .................................................. A61M 1/00
[52] U.S. Cl. ........................ 604/332; 604/361; 206/459.1
[58] Field of Search .................................. 604/332, 333, 604/361, 362; 383/1, 5; 206/459.1, 524.7

[56] References Cited

U.S. PATENT DOCUMENTS

| | | | |
|---|---|---|---|
| 3,209,977 | 10/1965 | Lewis et al. | 383/1 |
| 4,522,738 | 6/1985 | Magid et al. | 252/103 |
| 4,998,666 | 3/1991 | Ewan | 383/5 |
| 5,064,664 | 11/1991 | Hustad | 206/459.1 |
| 5,403,299 | 4/1995 | Schneider | 604/332 |

*Primary Examiner*—John G. Weiss
*Assistant Examiner*—Mark O. Polutta
*Attorney, Agent, or Firm*—Tilton Fallon Lungmus

[57] ABSTRACT

A flush-interval indicator for soluble, toilet bowl discardable pouches is disclosed for indicating to a user, once the pouch is discarded in a toilet bowl, when a sufficient flush-interval has elapsed so that, when the toilet is then flushed, the pouch will quickly disintegrate without obstructing or impeding the flow of water and waste material through the discharge lines of the system. The flush-interval indicator comprises optically-distinguishable indicia printed or otherwise affixed to a display surface of a pouch and normally concealed by a water-soluble opaque layer. The opaque layer may take the form of an external panel secured to the pouch, or a water-soluble layer of the pouch itself which includes pigment to render it opaque and shield the indicator from view. In an alternate construction, a water-soluble external cover is secured to the pouch and fibers from the cover are heat sealed into the pouch's display surface to form a flush indicator that is relatively unreadable when the cover is dry. However, when the pouch is exposed to water, the cover dissolves or disperses, after a sufficient flush-interval has elapsed, to reveal the flush indicator formed from the embedded fibers.

4 Claims, 1 Drawing Sheet

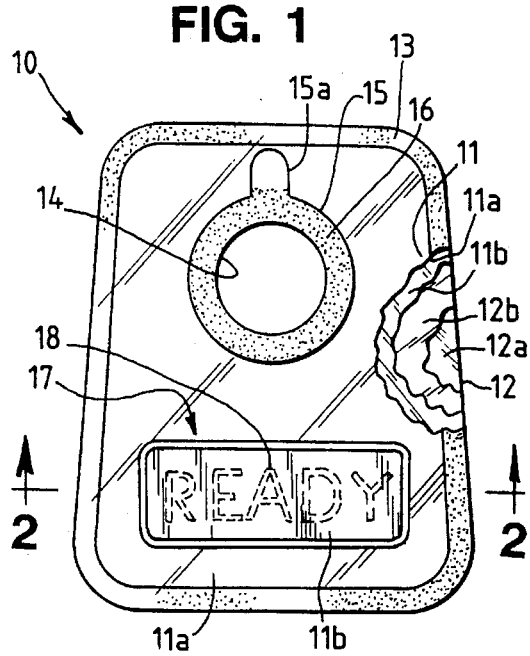
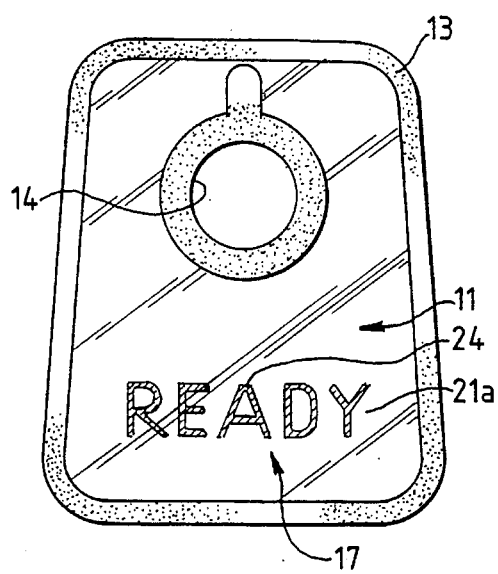
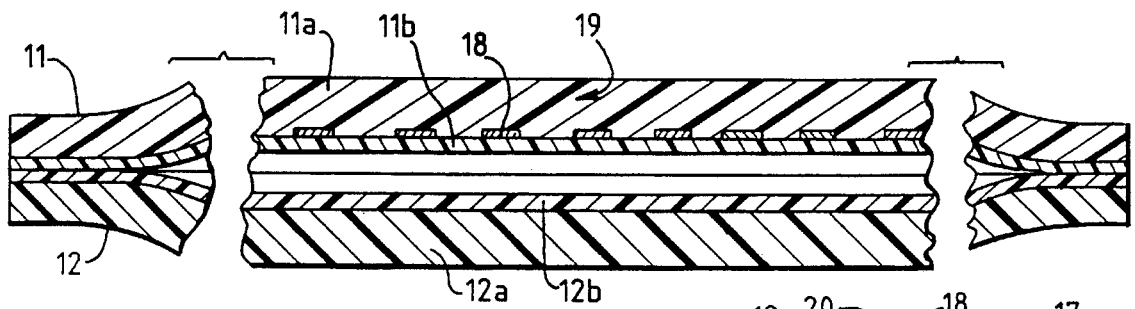
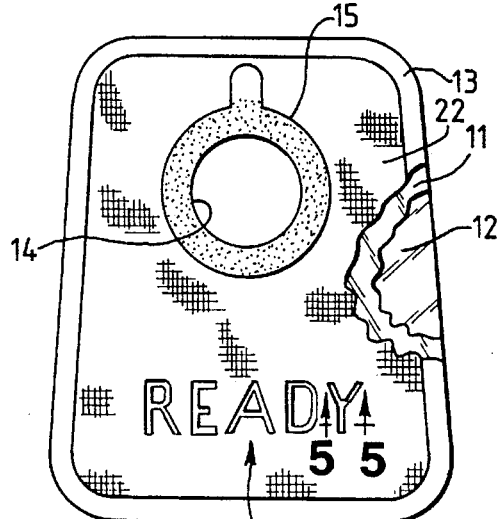
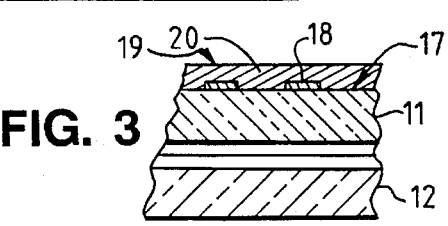
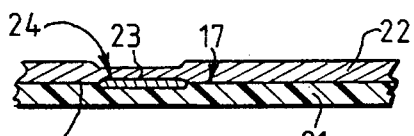

FLUSH-INTERVAL INDICATOR FOR SOLUBLE POUCHES

This is a division of application Ser. No. 08/184,220, filed Jan. 18, 1994, now U.S. Pat. No. 5,403,299.

BACKGROUND AND SUMMARY

Soluble pouches, particularly ostomy pouches, are known which may be discarded and dissolved (or dispersed) in the water of a common toilet bowl and in the discharge lines of a water-disposal system. One type of such a pouch is at least partially formed of pH-sensitive material so that an alkali or acidic agent can be added to the toilet bowl to initiate dissolution of the pouch (see U.K. patent application GB 2,201,372A and U.S. Pat. No. 4,620,999). Another type of known flushable pouch is constructed of a pair of side walls that are each composed of at least two layers, specifically, a tough, flexible, but water-soluble or water-dispersible primary layer, which gives the pouch its structural integrity and a thin, water-insoluble inner layer which lines the inside of the pouch and prevents the pouch's contents from contacting and dissolving the primary layer when the pouch is worn (see U.S. Pat. Nos. 4,772,279 and 4,917,688). For effective results, both types of pouches typically require a waiting interval between the time a pouch is discarded in the bowl and the time the toilet is flushed; otherwise, the pouch may not have dissolved sufficiently to be discharged by the flushing operation and might even cause at least temporary obstruction of the toilet and/or waste discharge lines. It is therefore believed that some type of flush-interval indicator would be useful to help prevent a user from prematurely flushing a toilet after discarding a pouch in the toilet bowl and also to inform the user when a sufficient time interval has elapsed and further waiting is unnecessary. The time period of such a flush-interval will vary depending upon the particular type of soluble pouch involved but, in general, a waiting period of at least 30 seconds, but not exceeding 5 minutes, preferably no more that 3 minutes, is typical. It is believed that any type of flush-interval indicator that would require effort or active participation on the user's part would tend to be ineffective because of inconvenience and resulting non-use. Such considerations render unrealistic any sort of timing mechanism or accessory that would be operated by the user such as providing the user with a chemical that, when poured into the toilet bowl, would change color after a sufficient flush-interval has elapsed.

An important aspect of this invention therefore lies in providing a relatively uncomplicated flush-interval indicator that does not require any active participation on the part of the user and is self-contained in that the indicator is integral with the pouch and does not require the user to carry any additional timing means, chemical packets, or the like. Such a flush-interval indicator comprises a flushable, soluble pouch having a pair of side walls joined together along their outer margins and having a display surface on at least one of its side walls. An optically-distinguishable flush indicator is printed upon or otherwise affixed to a display surface of the pouch for visibly indicating to a user when a sufficient flush-interval has elapsed after the user has discarded a pouch in a toilet bowl. The indicator may take the form of words such as "READY", "FLUSH", or the like, which provide a visible signal to the user when the pouch should be flushed. A water-soluble concealing means is positioned to shield the indicator from view when the pouch is dry. However, the concealing means, when exposed to water in a toilet bowl for an interval of about 30 seconds to a maximum of 5 minutes, preferably no longer than 3 minutes, is capable of dissolving or dispersing sufficiently to reveal the flush indicator.

In one embodiment, the flushable pouch is constructed of a pair of side walls that are each comprised of a primary layer of strong but water-soluble material capable of quickly dissolving in the water of a toilet bowl and a protective inner layer of relatively weak but water-insoluble material which protects the primary layer from the contents of the pouch. In that embodiment, the flush indicator is printed on the water-insoluble inner layer, and the concealing means comprises a water-soluble primary layer which is opaque or contains a pigment to render it opaque. When a user discards the pouch in a toilet bowl, the water-soluble primary layer sufficiently dissolves or disperses, after a predetermined interval, to reveal the indicator printed upon the inner layer, thereby visibly signaling the user that the toilet may be safely flushed. Such a construction is particularly effective as the flush-interval, the time it takes for the opaque layer to dissolve, coincides with the dissolution or dispersion of the primary layer of the pouch, and the indicator is only revealed once the pouch is in such a condition that it may be safely and effectively flushed away. In other embodiments, the side walls of the pouch may be formed of only a single layer and it may not be possible to use a water-soluble layer of the pouch itself as the means for concealing an indicator on the pouch. For such pouches, the concealing means may comprise an opaque external panel secured to the pouch to cover and shield the indicator from view when the opaque layer is dry. Depending upon the particular construction of the soluble pouch, the external panel may be made of material that will dissolve, when exposed to water, in a time period that corresponds with the interval needed for the soluble pouch to break down to such a degree that it may be effectively flushed away. Once again, it is believed that a time period of at least 30 seconds is desirable and, in some instances, such period may extend up to 3–5 minutes. The external panel may be formed of a cellulosic material, such as opaque paper. However, tissue paper has been found to be particularly effective as it is highly absorbent and hydrophilic in nature, which is believed to enhance the rate of dissolution of the pouch as it ensures that water in the toilet bowl is brought into and maintained in close contact with the pouch side walls. Forming the external panel of tissue paper is also advantageous in that it promotes patient comfort by providing a soft, absorbent layer next to the skin when the pouch is worn. It is also believed that such a tissue layer, when the toilet is flushed, helps to overcome film buoyancy problems by entrapping and pulling the pouch film, or fragments of pouch film, which may otherwise tend to float, into the discharge lines of the water-disposal system.

In an alternate construction, the side walls of the pouch may be formed of single or multiple layers and the concealing means comprises an opaque external cover formed of fibers which is secured to the pouch over a display surface provided by at least one of the side walls. The fibrous cover is adapted to quickly dissolve or disperse, after a sufficient flush-interval has elapsed, when exposed to water in a toilet bowl. The flush indicator is formed on the display surface of the pouch by embedding fibers of the cover into the display surface, preferably with a heat seal, to define a word such as "FLUSH", "READY", or the like. The indicator word is not distinguishable while the cover is in a dry state but, after the pouch has been discarded in the water of a toilet bowl and the external cover has sufficiently dissolved or dispersed, the fibers remaining embedded in the pouch provide a visible and legible indicator to signal the user that the pouch may be safely flushed.

3

Other features, advantages, and objects of the invention will become apparent from the specification and drawings.

DRAWINGS

FIG. 1 is a fragmentary plan view of a flushable pouch and flush-interval indicator of this invention.

FIG. 2 is an enlarged, somewhat schematic cross-sectional view taken along line 2—2 in FIG. 1.

FIG. 3 is an enlarged, somewhat schematic cross-sectional view of another embodiment of a soluble pouch and flush-interval indicator of this invention.

FIG. 4 is a fragmentary plan view of another embodiment of a flushable pouch and indicator of this invention.

FIG. 5 is an enlarged, somewhat schematic cross-sectional view taken along line 5—5 in FIG. 4.

FIG. 6 is a plan view of the pouch and indicator of the embodiment shown in FIGS. 4 and 5 after the flush-indicator has been revealed.

DETAILED DESCRIPTION OF PREFERRED EMBODIMENTS

While the flush-interval indicator of this invention is described in connection with a flushable ostomy pouch, it will be understood that the indicator of this invention may be advantageously used with other types of pouches that are soluble and discardable in a toilet bowl. In FIGS. 1 and 2, the numeral 10 generally designates a soluble ostomy pouch which includes a pair of side walls 11 and 12 joined together along their outer margins by peripheral heat seal 13 or by any other suitable means. Depending upon the particular type of soluble pouch, walls 11, 12 may be formed of single or multiple layers of pH-sensitive materials, water dissolvable or dispersible materials, or other soluble materials which enable a user to at least initiate dissolution and disintegration of the pouch in the water of a common toilet bowl. FIGS. 1 and 2 depict one known type of soluble pouch that has each of its side walls 11, 12 composed of at least two layers, specifically, a primary layer 11a, 12a and a protective interior layer 11b, 12b. In each case, the primary layer 11a, 12a is formed of a material which is flexible and relatively tough and strong in a dry state but is soluble in cold water (i.e., water at room temperature) at either a neutral or an adjusted (i.e., raised or lowered) pH level. As used herein, the term "water-soluble" also includes materials that are water-dispersible. Thus, the primary layer might be formed of tissue paper or other similar cellulosic materials that provide substantial strength when dry, but disintegrate quickly when exposed to water. However, in general, it is believed preferable to form primary layers 11a, 12a of plastic films composed of water-soluble polymers such as polyvinyl alcohol, methyl hydroxypropyl cellulose, polyethylene oxide, or carboxymethyl cellulose.

Primary layers 11a, 12a provide structural integrity to pouch 10 when the appliance is worn. In contrast, the interior layers 11b, 12b are relatively thin and weak, serving essentially as protective coatings to prevent direct exposure of the primary layers to the contents of the pouch. Because of their composition and/or thinness, interior layers 11b, 12b lack sufficient strength to maintain the integrity of the pouch when the primary layers 11a, 12a have been dissolved or dispersed. Hence, the walls of the pouch, when exposed to the water and turbulence in a flushed toilet, readily disintegrate. The interior layers or coatings may be formed of polyvinylidene chloride, atactic propylene nitrocellulose, or any other suitable water-insoluble material.

Side wall 11 has an opening 14 therethrough which defines a side opening or stoma receiving opening for the pouch. In the illustration given, the pouch 10 is one component of a two-piece ostomy appliance, the other component being an adhesive faceplate (not shown) that may be adhesively secured to the peristomal skin surfaces of a patient. An external mounting ring 15 circumscribes the pouch opening and is coated along its outer surface (i.e., the surface facing away from the pouch) with an annular layer 16 of pressure sensitive adhesive. Mounting ring 15 may be provided with one or more peripheral extensions or tabs 15a which project radially outward beyond the remaining periphery of the mounting ring. Tab 15a is provided so that a user may readily grip the tab as the pouch is being manipulated to secure the mounting ring to the faceplate or detach it from that faceplate. A particularly effective faceplate component, which includes a smooth annular surface for sealingly engaging the adhesive layer 16 of the ring 15 and has a protective annular flange for preventing premature disintegration of the exposed edges of the pouch walls around the opening 14, is disclosed in co-owned pending application Serial No. 042,008. It is to be understood that while pouch 10 has been shown and described as one component of a two-piece appliance, it may instead constitute the sole element of a one-piece appliance, in which case mounting ring 15 would constitute an integrated faceplate for direct adhesive attachment to the peristomal skin surfaces.

An outwardly facing display surface, generally designated at 17, is provided on at least one of the side walls (shown on side wall 11 in FIG. 1), and an optical flush indicator 18 is printed on or otherwise applied to display surface 17 for indicating to a user when a sufficient flush-interval has elapsed after the pouch has been discarded into the water in a toilet bowl. Indicator 18 may take the form of the word "READY" as shown, or other indicia such as "FLUSH", "SAFE", color coded symbols or the like, all of which convey to a user that the pouch is ready to be flushed away. Indicator 18 can be formed from common indelible ink and can be printed on the display surface during pouch manufacture. When the pouch side walls are formed of a water-soluble primary layer 11a, 12a and a protective, water-insoluble inner layer 11b, 12b, indicator 18 is preferably printed on the inner layer which, being water-insoluble, will maintain enough integrity to display the indicator when the outer layer has partially dissolved or dispersed.

In the embodiments shown in FIGS. 1–3, water-soluble concealing means 19 in the form of an opaque layer is provided for covering display surface 17 and concealing indicator 18 while the pouch is being worn and until the pouch has been discarded in the water of a toilet bowl and a sufficient flush-interval has elapsed. The water-soluble opaque layer is capable, when exposed to water in a toilet bowl, of being sufficiently dissolved or dispersed when the flush-interval has elapsed to reveal indicator 18, thereby visably signaling to the user that the pouch is ready to be flushed away. When the pouch is composed of primary layers 11a, 12a and inner layers 11b, 12b (FIG. 2), the opaque layer may take the form of primary layer 11a which is composed of opaque material or contains pigment capable of rendering it opaque. It will be noted that most known polymeric materials for forming such a primary layer are generally translucent and known dyes or pigments may be added during the manufacturing process to render them opaque. Most cellulosic materials for forming the primary layers, such as tissue papers as used in toilet tissues and toweling, are already opaque and do not require the addition of a pigment or dye.

In the shown construction in FIG. 2, the flush-interval will be determined by the particular selection of materials, and the thickness of such materials, that form the primary layers of the pouch, but it is believed that most of such known materials require at least 30 seconds and, in some instances, 3 to 5 minutes for the layers to sufficiently disintegrate and reveal the indicator. It will be noted that such a construction is particularly advantageous as the opaque layer, which conceals the flush indicator, is formed from the primary structural layers of the pouch, and the flush indicator is therefore only revealed after the structural layers have sufficiently disintegrated such that the pouch may be safely and effectively flushed away.

In another embodiment shown in FIG. 3, walls 11, 12 are shown as being formed of a single layer, but they may also be comprised of single or multiple layers of pH-sensitive or otherwise soluble materials. Indicator 18 is shown as being printed on or otherwise affixed to the outer most surface of wall 11, but indicator 18 may also be printed at any point within wall 11 or 12, as long as the layers between indicator 18 and outer most surface of the pouch are translucent. In that embodiment, concealing means 19 takes the form of an opaque external panel 20 secured to the pouch along display surface 17 by a peripheral heat seal (not shown) or by other suitable means. External panel 20 shields indicator 18 from view when the panel is dry; however, when exposed to water in a toilet bowl, panel 20 dissolves or disperses, after a sufficient flush-interval has elapsed, to reveal indicator 18, thereby visibly signaling to the user that the pouch is ready to be flushed away. External panel 20 is preferably formed of tissue paper as it provides a soft layer which promotes patient comfort and enhances the rate of dissolution of the layers when the pouch is discarded in a flush toilet, since the highly absorbent and hydrophilic nature of such tissue paper is believed useful in ensuring that the soluble portions of the pouch are exposed to water. Suitable tissue papers should have a low wet-strength but should also have a rather heavy construction, and 20 pound basis weight tissue has been found to be particularly effective for forming external panel 20. However, external panel 20 may also be formed of other cellulosic materials, such as soluble paper, which are opaque and relatively strong when dry, but disintegrate quickly when exposed to water. One particularly effective water-soluble paper is commercially available from the Gilbreth International Paper Company, and is sold under the tradename Dissolvo 2800. It is also contemplated that other materials, such as polymers, may be used as long as the material is opaque and capable of quickly dissolving or dispersing when exposed to water in a toilet bowl. The material should also be selected so that the time interval for it to dissolve or disperse coincides with the interval required for sufficient disintegration of the pouch to occur so that it may be safely and effectively flushed away. It is believed that a flush-interval of about 30 seconds to 5 minutes should be provided, preferably no longer than 3 minutes. During the interval, the user can attend to other tasks associated with wearing an ostomy pouch such as cleaning the stoma area, preparing a new pouch or faceplate, and comfortably securing the new pouch to the peristomal skin surfaces or the faceplate.

FIGS. 4–6 depict another embodiment of this invention in which pouch 10 includes side walls 11, 12 which may be formed of single or multiple layers. Regardless of the particular construction of the side walls, at least one of the side walls includes an outer layer 21 (FIG. 5) which provides display surface 17 on its outermost surface 21a. In that embodiment, the concealing means takes the form of an external cover 22 which is formed of fibers 23 and secured to the pouch over display surface 17 by peripheral heat seal 13 or other suitable means. Although external cover 22 is shown as covering the entire side wall, the cover may also be of smaller proportions so that it only covers a finite area over display surface 17.

The optical flush indicator in this embodiment is formed from cover 22 by heat sealing or otherwise binding fibers 23 into layer 21 of the pouch, as most clearly seen in FIG. 5, to form a fibrous, legible flush indicator 24. Flush indicator 24 may take the form of indicator words such as "READY", "FLUSH", or the like, or other indicia which readily indicates to a user that the pouch is ready to be flushed. As shown in FIG. 4, flush indicator 24 is relatively unreadable and undistinguishable from cover 22 when the cover is dry. It will be noted that, when the cover is dry, indicator 24 may faintly appear on cover 22 as an embossed or slightly smooth region; however, such an appearance is readily distinguishable from the appearance of the indicator when the cover is wet. When the pouch is discarded in the water of a toilet bowl, cover 22 dissolves or disperses, after a sufficient flush-interval, so that only the fibers which are embedded into layer 21 and constitute flush indicator 24 remain on the display surface of the pouch to provide a visible and legible flush indicator 24 which signals to the user that the pouch may be safely flushed away (FIG. 5).

Cover 22 may be made of a cellulosic material, such as soluble paper, and one particularly effective soluble paper is sold under the trade name Dissolvo 1800 by Gilbreth Paper Company International. However, it is believed that forming cover 22 of a tissue paper is preferable as it promotes patient comfort and enhances the rate of dissolution of the water-soluble components of the pouch. It will be noted that in some circumstances, outer layer 21 of the pouch may be made of water-soluble or otherwise dispersible materials, but it is believed that heat sealing fibers 23 into the layer will enable that portion of the layer to maintain enough integrity to display the indicator even as the rest of the layer dissolves or disperses in the water of the toilet bowl.

While in the foregoing, embodiments of the invention have been disclosed in considerable detail for purposes of illustration, it will be understood by those skilled in the art that many of these details may be varied without departing from the spirit and scope of the invention.

We claim:

1. The combination of a pouch and a flush indicator comprising:

a flushable, soluble pouch having a pair of side walls joined together along their outer margins and having a display surface on at least one of said side walls;

a water-soluble external cover formed of fibers and secured to said pouch over said display surface; and a flush indicator formed of fibers of said external cover which are embedded into said display surface of said pouch, said flush indictor being relatively undistinguishable from said external cover when said cover is dry, said external cover, when exposed to water in a toilet bowl, being capable of quickly dissolving or dispersing, after a sufficient flush-interval has elapsed, to reveal the fibers of said indicator which remain embedded in said display surface when said cover dissolves or disperses, thereby visibly signaling to a user that said pouch is ready to be flushed.

2. The combination of claim 1 in which said embedded fibers of said indicator are heat-sealed into said display surface of said pouch.

3. The combination of claim 1 in which said cover is formed of cellulosic material.

4. The combination of claim 3 in which said cover is formed of water-soluble tissue paper of heavy basis weight but having low wet-strength.

* * * * *